United States Patent [19]
Wright et al.

[11] Patent Number: 5,267,381
[45] Date of Patent: Dec. 7, 1993

[54] AUTOMATIC TUBE PROCESSING SYSTEM

[75] Inventors: William M. Wright, North Huntingdon; William J. Bloom, Middle Taylor Township, Cambria County; Mark A. Troxell, Homer City; Kevin W. Kutchenriter, Unity Township, Westmoreland County, all of Pa.

[73] Assignee: Westinghouse Electric Corp., Pittsburgh, Pa.

[21] Appl. No.: 656,371

[22] Filed: Feb. 19, 1991

[51] Int. Cl.$^5$ .............................................. B23B 5/16
[52] U.S. Cl. ................................... 29/33 T; 82/1.11; 82/48; 356/376
[58] Field of Search .............. 29/33 T, 33 D; 82/1.11, 82/48, 86, 46, 70.1, 70.2, 98, 113; 356/376

[56] References Cited

U.S. PATENT DOCUMENTS

| | | | |
|---|---|---|---|
| 3,612,890 | 10/1971 | Cornyn, Jr. et al. | 356/376 X |
| 3,635,108 | 1/1972 | Prince | 82/173 X |
| 3,791,466 | 2/1974 | Patterson et al. | 176/78 |
| 4,199,258 | 4/1980 | Dau | 356/378 |
| 4,561,333 | 12/1985 | Kohno et al. | 82/1.11 |
| 4,634,879 | 1/1987 | Penney | 356/376 X |
| 4,893,932 | 1/1990 | Knollenberg | 356/369 |
| 4,902,131 | 2/1990 | Yamazaki et al. | 356/336 |
| 4,908,517 | 3/1990 | Imamura | 250/563 |
| 4,926,050 | 5/1990 | Shemwell | 250/560 |

FOREIGN PATENT DOCUMENTS

| | | | |
|---|---|---|---|
| 0198557 | 10/1986 | European Pat. Off. | 356/376 |
| 0111401 | 7/1982 | Japan | 356/376 |
| 0216905 | 12/1983 | Japan | 356/376 |
| 0080010 | 4/1986 | Japan | 356/376 |

OTHER PUBLICATIONS

"New .0001" Laser Measurement Resolution ... with Aromat Triple Beam Technology, Oct. 1990, vol. 7, No. 11, of *Sensors, The Journal of Machine Perception* magazine, advertisement by Aromat Corporation.

"See the Difference!", Oct. 1990, p. 96 of *Quality* magazine, advertisement by Keyence Corporation of America.

*Primary Examiner*—Z. R. Bilinsky
*Attorney, Agent, or Firm*—Aileen Addessi

[57] ABSTRACT

The automatic tube processing system and method utilizes an automatic laser inspection system capable of inspecting the face of a tube for defects during the manufacturing process of the tube. The automatic tube processing system and method comprises a light source, such as a laser, positioned near a tube for transmitting light onto the face of the tube. The tube and the light source may be rotated relative to one another to enable the entire face of the tube to be inspected. An electrical receiver for detecting light reflected from the face of the tube is positioned near the light source. The electrical receiver is capable of determining a height differential on the face of the tube and capable of producing an output to be analyzed by a processing means. A monitor displays the output from the processing means in the form of a graph.

26 Claims, 6 Drawing Sheets

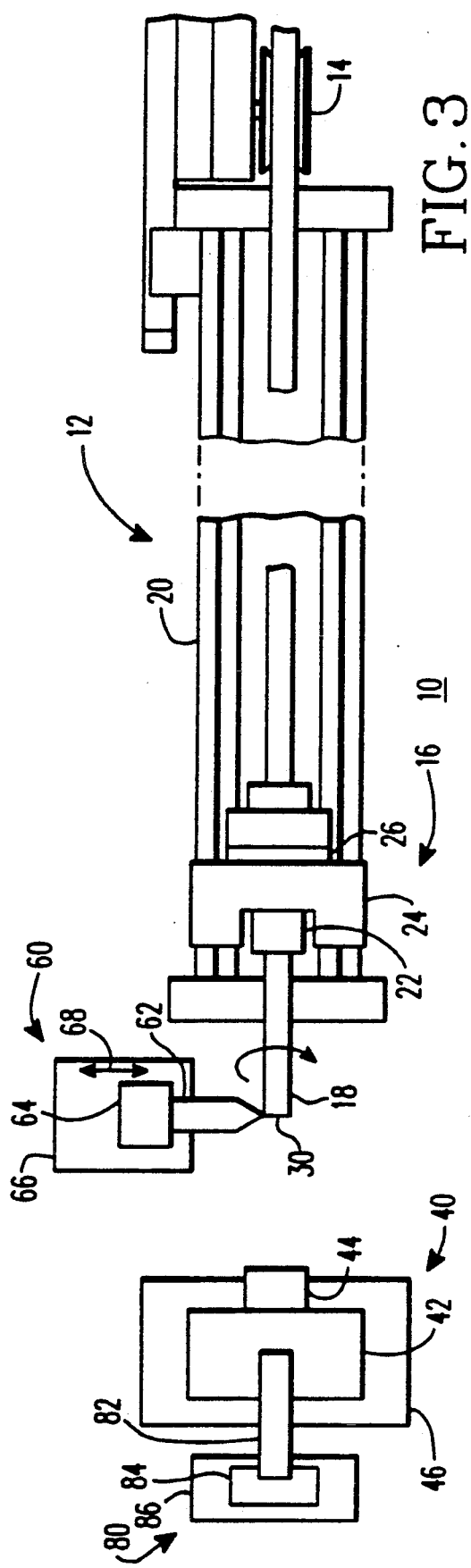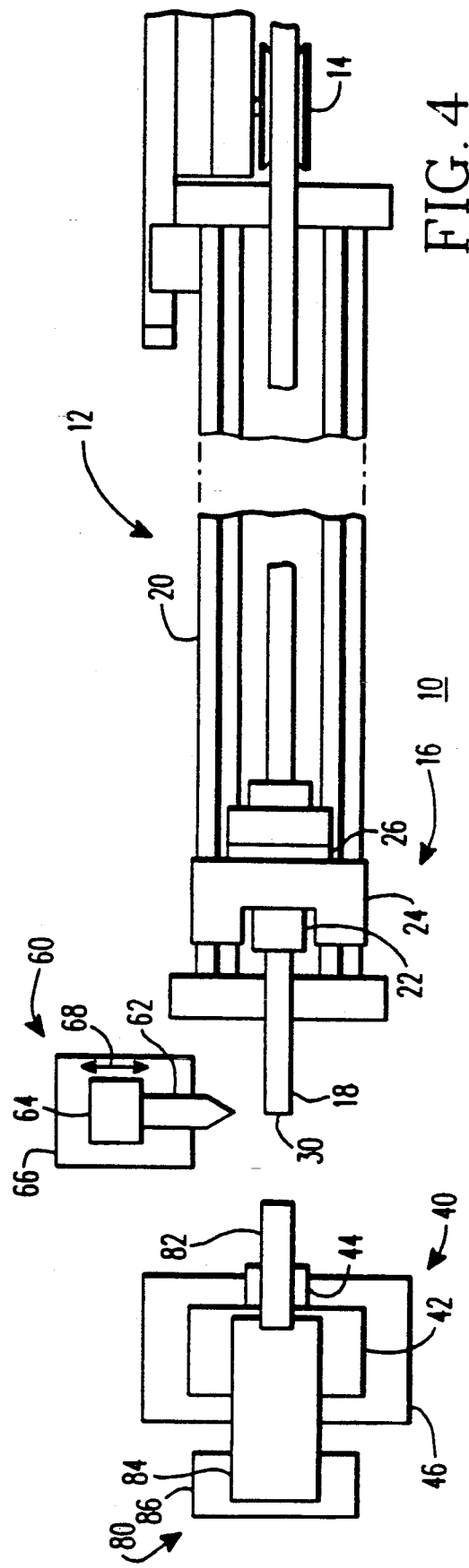

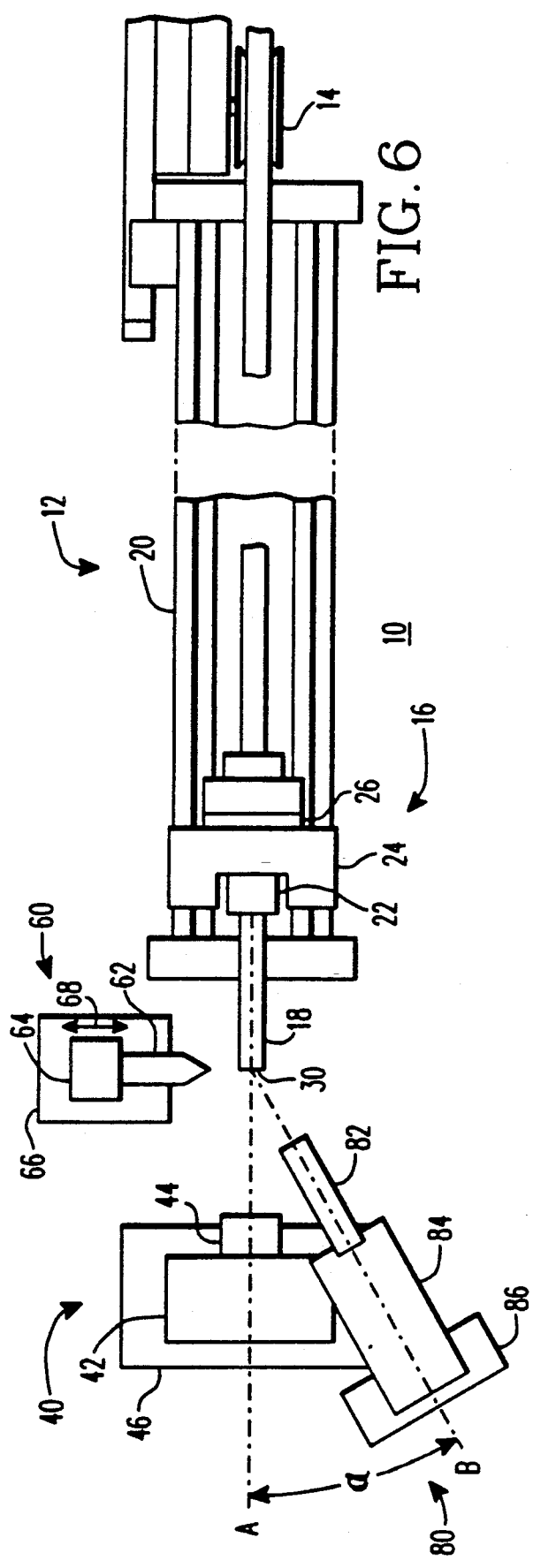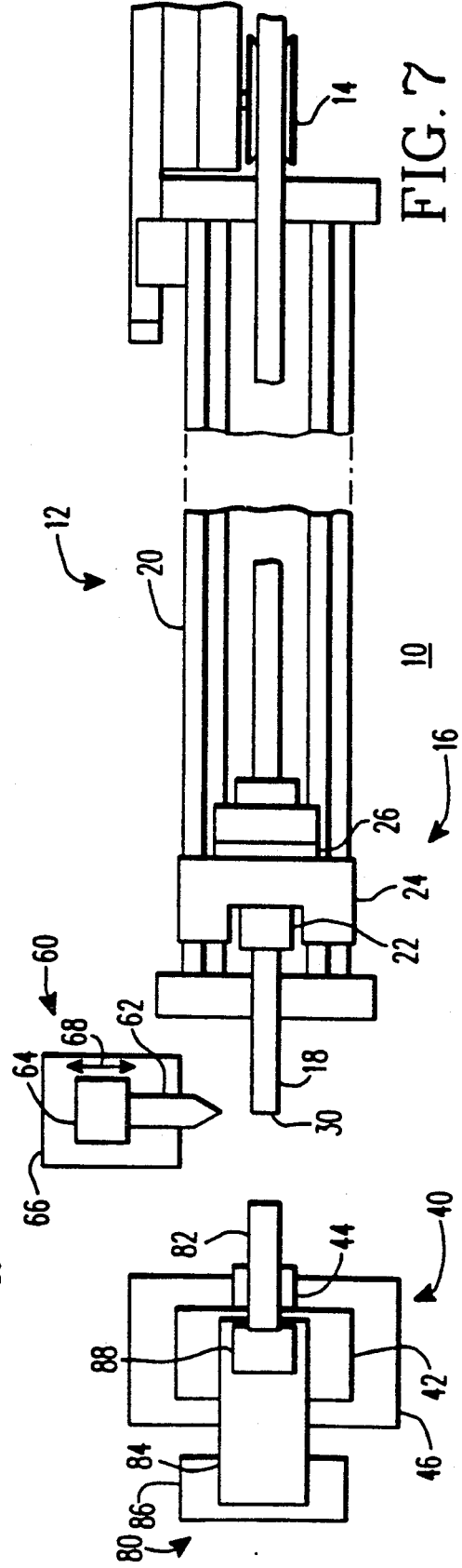

AUTOMATIC TUBE PROCESSING SYSTEM

BACKGROUND OF THE INVENTION

This invention relates to the inspection of a face of a tube, and more particularly, to an automatic tube processing system and method for preparing and inspecting the face of a tube, for use in nuclear fuel assemblies, during the manufacture of the tube.

Several procedures are performed during the manufacturing process of a tube, such as cutting the tube to a desired length, finishing the face of the tube, and inspecting the face of the tube for defects, such as scratches, chatter, steps, nicks, burrs, and out of squareness.

Tubes may be utilized for various uses and in various applications, such as in nuclear fuel assemblies. U.S. Pat. No. 3,791,466, issued Feb. 12, 1974 to Patterson et al., describes several types of thin walled tubing used in nuclear fuel assemblies, such as the nuclear fuel tube within which nuclear fuel pellets are housed during operation of the nuclear reactor, the guide thimble tube which provides structure to the nuclear fuel assemblies and houses the control rods within the nuclear reactor, the instrumentation tube which contains various instruments housed within the nuclear reactor, and the tube for containing an internal burnable absorber rod which regulates the power within the nuclear reactor core.

Currently, during the manufacturing process of a tube, the tube is advanced by an advancing mechanism to a rotatable collet, which grips and rotates the tube. A motor is connected to the collet to provide the rotation for the collet. When a solenoid is activated, a movable stop extends from the solenoid to a predetermined distance, pushing the tube through the collet to a desired position. The collet grips the tube, while rotating, in this position. A cutting bit advances toward the tube and cuts the tube to a desired length. The cutting bit may also make a second cut to perform the finishing process on the face of the tube.

After the cutting and finishing processes, the tube is inspected for defects on the face of the tube. One approach to inspecting the face of the tube is for an individual to shine a flashlight onto the face of the tube in a circular manner to visually inspect the tube face. However, because this approach is performed manually, it is time consuming.

Another approach to inspecting the face of the tube is for an individual to visually check the surface of the face of the tube with a magnifying glass. Also, the individual may use a plug gauge to check for burrs on the inside diameter of the tube and may use a dial indicator to check for out of squareness on the face of the tube. However, because these approaches do not provide a complete inspection of the face of the tube, an additional inspection step, such as the above mentioned approach, is also used in the inspection process.

Currently, approximately 1 out of 15 tubes may be preliminarily inspected with a plug gauge, a dial indicator, and a magnifying glass by an individual. If the tube passes this preliminary inspection, then the tube is moved to a different location within the manufacturing facility for the next stage of the manufacturing process of the tube. After the manufacturing process is complete and the tube is ready for shipment, the final inspection is performed. At this final inspection stage, every tube is visually inspected by an individual shining a flashlight onto the face of the tube in a circular manner and by using a plug gauge and dial indicator. If a defect, such as a scratch, chatter, step, nick, burr or out of squareness is discovered on the face of the tube, then the tube will have to be reworked, requiring removal of the tube from this location in the manufacturing facility to the location in the facility for performing the cutting and finishing processes. Because only 1 out of 15 tubes may be preliminarily inspected at the finishing stage, possibly a defect may be discovered upon final inspection on the face of any of the tubes that were not preliminarily inspected at the finishing stage. Also, if a tool used in the manufacturing process was damaged, the tool may have caused defects in a number of tubes, requiring a large number of tubes to be reworked.

Therefore, the disadvantages to the above mentioned approaches are that to perform these inspections on every tube visually and manually by an individual at the time of finishing the face of the tube while the tube remains positioned at the finishing stage is time consuming. To selectively inspect a percentage of the tubes, such as 1 out of 15 tubes, at the finishing stage of manufacture creates the possibility of defective tubes being processed through the manufacturing operation until the defects are discovered at the final inspection. To perform the inspection of every tube at the final stage of manufacturing is also time consuming because if a defect is discovered on the face of the tube, the tube must be transported from the final inspection location to the cutting location within the facility and must be reworked from the cutting stage through to the final inspection until the defects no longer exist.

Therefore, what is needed is an apparatus and method that automatically inspects the face of a tube efficiently and economically, while the tube is still in the manufacturing process, preferably while positioned at the finishing stage of manufacture, to increase productivity.

SUMMARY OF THE INVENTION

The automatic tube processing system and method utilizes an automatic laser inspection system capable of inspecting the face of a tube for defects during the manufacturing process of the tube. The automatic tube processing system and method comprises a light source, such as a laser, positioned near a tube for transmitting light onto the face of the tube. The laser may focus a visible light spot on the face of the tube for enabling an individual to visually observe the light spot on the face of the tube. Because the light spot may not focus on the entire face of the tube, the tube or the light source may be rotated relative to one another. An electrical receiver for detecting light reflected from the face of the tube is positioned near the light source. The electrical receiver is capable of determining a height differential on the face of the tube and capable of producing an output to be analyzed by a processing means. A monitor displays the output from the processing means in the form of a graph. The automatic tube processing system may also comprise a cutting tool positioned near the tube for cutting the tube, a facing tool for finishing the face of the tube, and a movable stop arranged near the face of the tube for positioning the tube in a cutting position.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings, wherein:

FIG. 3 is a plan view of the automatic tube processing system with the tube in a cut position;

FIG. 4 is a plan view of the automatic tube processing system with the cutting mechanism retracted to a resting position and an automatic laser inspection system positioning a light source to transmit light onto the face of the cut tube;

FIG. 6 is a plan view of the automatic tube processing system depicting an alternative positioning of the light source for transmitting light onto the face of the cut tube and of an electrical receiver for detecting light reflected from the face of the cut tube;

FIG. 7 is a plan view of the automatic tube processing system depicting an alternative manipulation means for rotating the light source relative to the tube;

DESCRIPTION OF THE PREFERRED EMBODIMENT

The invention described herein provides an automatic tube processing system and method which utilizes an automatic laser inspection system capable of inspecting the face of a tube during the manufacturing process of the tube.

Figure 1:
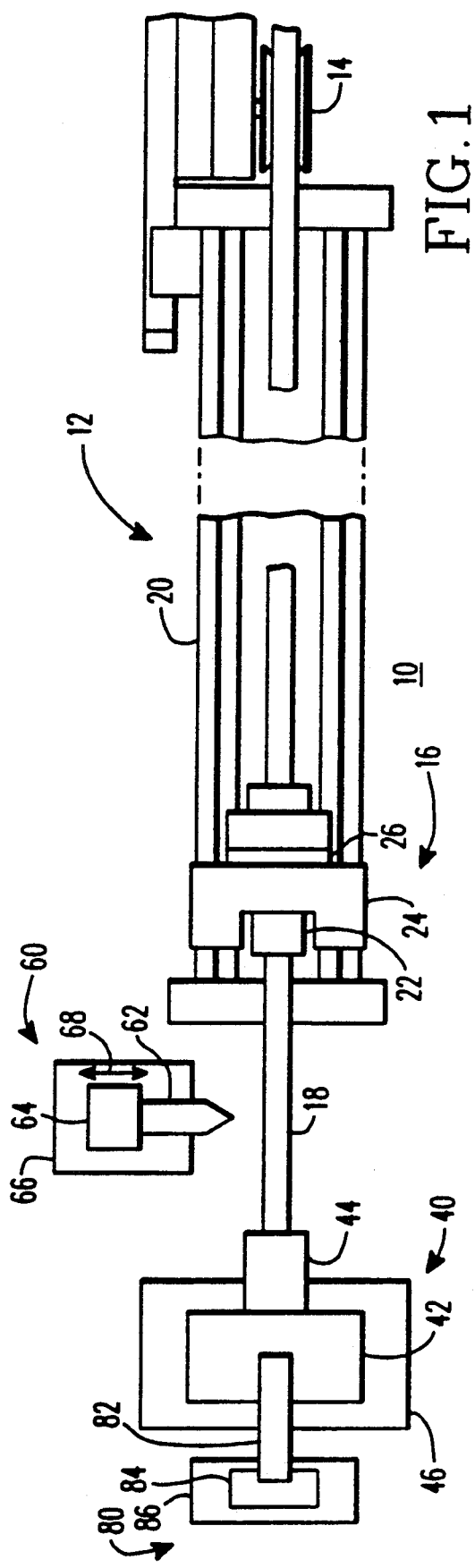
FIG. 1 is a plan view of an automatic tube processing system with a tube being positioned in a collet by an automatic stop mechanism.
Figure 2:
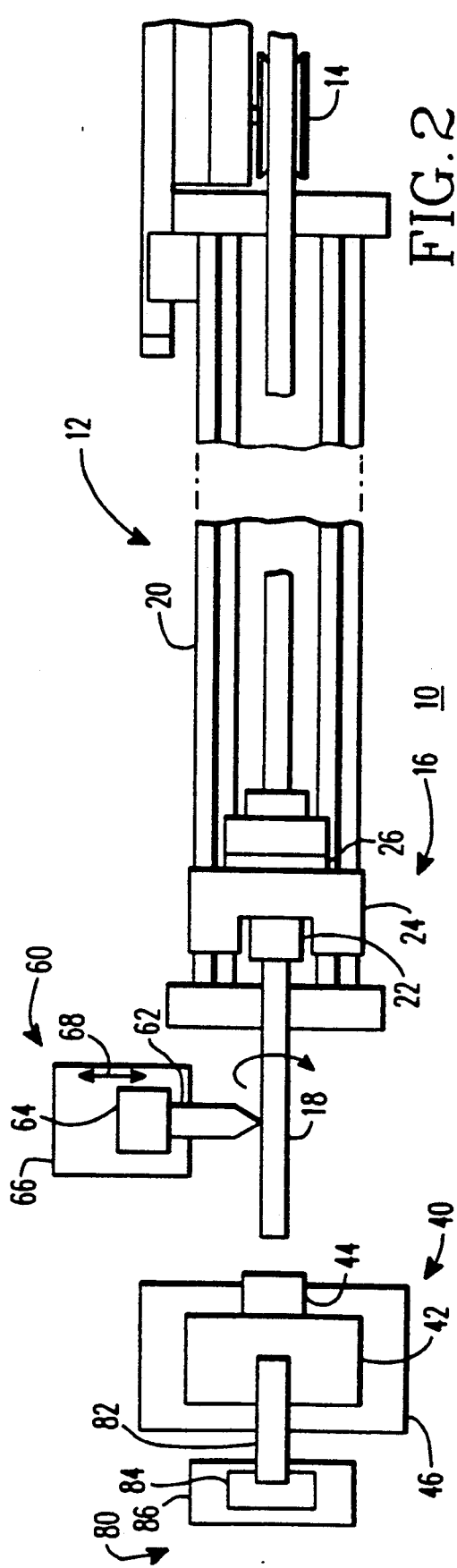
FIG. 2 is a plan view of the automatic tube processing system with the automatic stop mechanism retracted to a resting position and a cutting mechanism aligning a cutting tool with the rotating tube to begin the cutting stage of manufacturing the tube.

Referring to FIG. 1, an automatic tube processing system referred to generally as 10, comprises a tube support and positioning mechanism 12. Tube support and positioning mechanism 12 comprises an advancing mechanism 14 located at one end and a gripping and rotating mechanism 16 located at an opposite end of the tube support and positioning mechanism 12. Advancing mechanism 14, which may rotate, receives tube 18 at an entrance end and advances tube 18 along track 20 to the gripping and rotating mechanism 16. Tube 18 may be of a type used for various applications, such as a tube for use in a nuclear fuel assembly. Nuclear fuel assemblies utilize tubes as described in U.S. Pat. No. 3,791,466, such as nuclear fuel tubes for containing nuclear fuel pellets, thimble tubes for providing structural support to a nuclear fuel assembly and for housing control rods and other core components within a nuclear reactor, instrumentation tubes for housing instruments within a nuclear reactor, and internal burnable absorber tubes for regulating power within a nuclear reactor. Track 20, which is anchored to the ground, extends the length of tube support and positioning mechanism 12 and provides structural reinforcement for the advancing mechanism 14 and the gripping and rotating mechanism 16. The gripping and rotating mechanism 16 comprises a collet 22, which may be rotatable, for gripping and supporting tube 18 during the manufacturing process. Collet 22 is connected to track 20 by a first mounting member 24 at a height sufficient so that tube 18, which is advancing through the advancing mechanism 14, may be received in collet 22. The gripping and rotating mechanism 16 also comprises a motor 26 for rotating collet 22 during the manufacturing process. Motor 26 may be a motor manufactured by Bodine Gear Motor Co. with 1/12 hp and the capability of rotating at 30 revolutions per second. Motor 26, which is connected to collet 22 for rotating collet 22, is connected to first mounting member 24 for support of motor 26 during the manufacturing process of tube 18.

Figure 5:
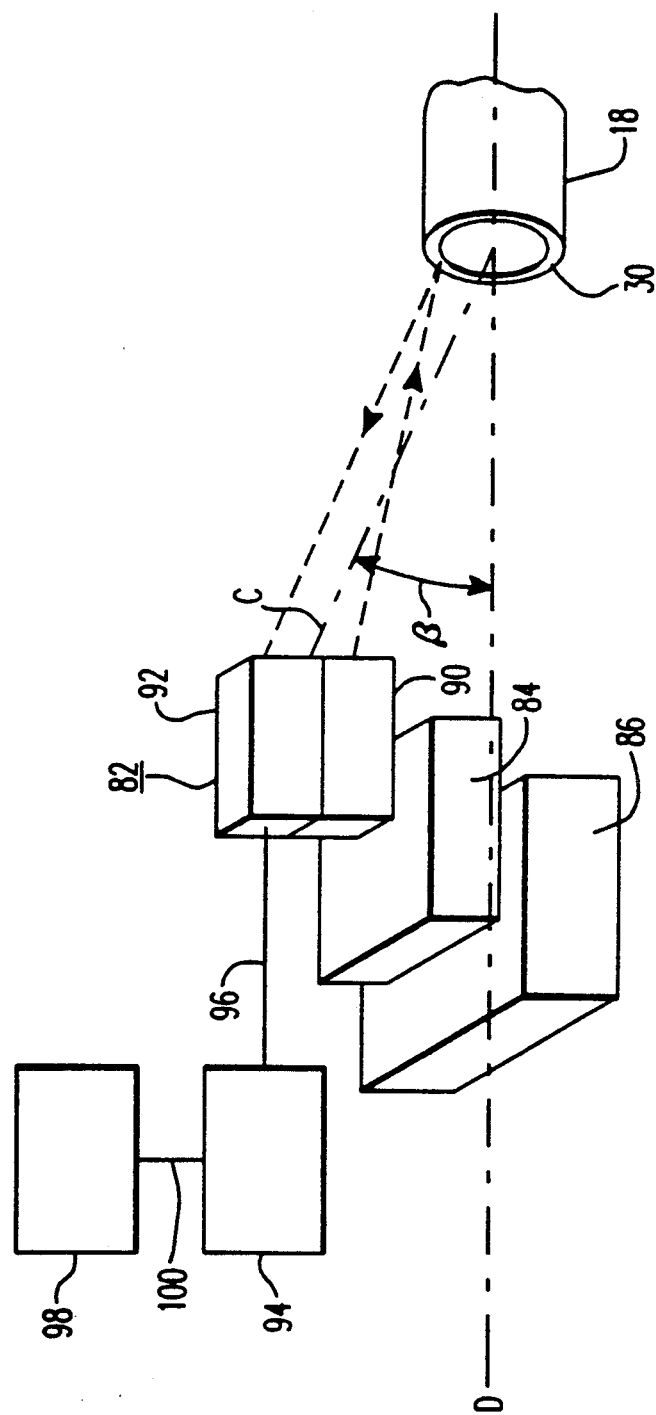
FIG. 5 is a side elevational view of the automatic laser inspection system with a transmitter directing light onto the face of the tube, an electrical receiver detecting the light reflected from the face of the tube, and electrical lines connecting the electrical receiver to a processing means and a monitor.

Referring to FIG. 3 and FIG. 5, tube 18 has a face 30, at an end of tube 18, defined by an inside diameter of tube 18 and an outside diameter of tube 18 and corresponding to the thickness of the wall of tube 18.

Referring to FIGS. 1–4, the automatic tube processing system 10 also comprises an automatic stop mechanism 40, positioned near a face 30 of tube 18. The automatic stop mechanism 40 comprises a solenoid 42, chosen from those well known in the art, such as a solenoid from Bodine Gear Motor Co. Solenoid 42 comprises movable stop 44 for positioning tube 18 in collet 22. When solenoid 42 is activated, movable stop 44 moves to and from tube 18, which is held in the gripping and rotating mechanism 16. The automatic stop mechanism 40 is arranged so that when movable stop 44 extends to tube 18, movable stop 44 is at a position where movable stop 44 is aligned with the longitudinal axis of tube 18 and is at a height sufficient for movable stop 44 to touch tube 18. When activated, movable stop 44 is extended from solenoid 42 to a predetermined distance, pushing tube 18 through collet 22 to a desired position. This predetermined distance is determined by calculating the usable or desired length of tube 18 and the length of the tube to be cut off of tube 18. Once tube 18 is positioned by movable stop 44, tube 18 is in a position to be out to the usable length. To provide structural support for solenoid 42, solenoid 42 is anchored to a first base 46, which is anchored to the ground so as to be substantially stable.

Still referring to FIGS. 1–4, the automatic tube processing system 10 also comprises a cutting mechanism 60. Cutting mechanism 60 is positioned near tube 18 so that the cutting mechanism 60 is arranged for cutting tube 18 to a usable length. Cutting mechanism 60 comprises cutting bit 62, which is a tool that can be used for cutting and finishing the face 30 of tube 18. Cutting bit 62 can be used as a cutting tool to cut tube 18 to a desired length. After cutting bit 62 has cut tube 18 to a usable length, cutting bit 62 can also be used as a facing tool to finish the face 30 of tube 18 by making a second cut on the face 30 of tube 18. Cutting bit 62 is attached to a second mounting member 64 for structural support of the cutting bit 62 and is positioned on the second mounting member 64 at a height sufficient so that cutting bit 62 is at substantially the same level as tube 18 to enable the cutting bit 62 to cut and finish tube 18. Second mounting member 64 is slidably mounted to a second base 66 for structural support of the second mounting member 64. As depicted by arrows 68, second mounting member 64 can be slid forward to allow cutting bit 62 to cut and finish tube 18 and can be slid backward to a non-cutting or rest position. Second base 66 is anchored to the ground to provide structural support so as to be substantially stable. Second base 66 is positioned near tube 18 to enable cutting mechanism 60 to cut and finish tube 18.

Still referring to FIGS. 1-4, the automatic tube processing system also comprises an automatic laser inspection system 80. The automatic laser inspection system 80 comprises a light source 82, which is positioned near the face 30 of tube 18 so that light can be transmitted from light source 82 onto the face 30 of tube 18. Light source 82 is attached to extendable member 84. Extendable member 84 provides structural support for light source 82 when light source 82 is not in use. When light source 82 is utilized for inspecting the face 30 of tube 18, extendable member 84 is capable of extending for positioning light source 82 to within approximately 2" from the face 30 of tube 18. When in the extended position, extendable member 84 also provides structural support for the light source 82. The close proximity of light source 82 to the face 30 of tube 18 is preferable for accurate results from the automatic laser inspection system 80. Extendable member 84 is mounted on a third base 86 at a position so that extendable member 84 can be extended to position the light source 82 to within a desired distance from the face 30 of tube 18. As an example, the extendable member 84 may be extended either over the top of the automatic stop mechanism 40 (as illustrated in FIG. 1) or extended beside the automatic stop mechanism 40 (as illustrated in FIG. 6). Third base 86 provides structural support for extendable member 84 and light source 82. Third base 86 is anchored to the ground so as to be substantially stable.

Still referring to FIGS. 1-4, the automatic laser inspection system 80 may be positioned so as to be substantially aligned with the longitudinal axis of tube 18. This positioning of light source 82 may be preferential because light is transmitted onto the face 30 of tube 18 along the longitudinal axis of tube 18 and is reflected from the face 30 of tube 18 back to light source 82 along the longitudinal axis of tube 18.

Referring to FIG. 6, as an alternative to the positioning of the automatic laser inspection system 80 as illustrated in FIG. 1, the automatic laser inspection system 80 may be positioned at an angle from plane A, where plane A is a substantially vertical plane which lies approximately along the longitudinal axis of tube 18. This alternative positioning of the automatic laser inspection system 80 may be necessary due to inadequate space available for positioning light source 82 along the longitudinal plane of tube 18. The automatic laser inspection system 80 may be positioned so that the light transmitted from light source 82 may be directed within an angle alpha defined by plane B, where plane B is a substantially vertical plane which lies approximately along the centerline of light source 82, and substantially vertical plane A, where plane A lies approximately along the longitudinal axis of tube 18, where angle alpha does not exceed approximately 5 degrees. Preferably, angle alpha should be 0 degrees.

Referring to FIG. 5, light source 82 is positioned so that the light transmitted from light source 82 may be directed within an angle beta defined by plane C, where plane C is a substantially horizontal plane which lies approximately along the centerline of light source 82 and plane D, where plane D is a substantially horizontal plane which lies approximately along the longitudinal axis of tube 18, where angle beta does not exceed approximately 45 degrees. The positioning of light source 82 between the above mentioned angles provides accurate output from automatic laser inspection system 80.

Light source 82 may be an invisible infrared laser, but it is preferable to use a visible light beam laser, such as a Red 670 nm Wavelength Visible Laser from Keyence Corporation of America. Preferably, the width of the visible light beam will be at least as wide as the thickness of the wall of the face 30 of tube 18 to enable the entire width of a portion of the wall of the face 30 of tube 18 to be inspected. By using a visible light beam laser, an individual may focus the light beam on the face of the tube and will be able to visually observe the light spot on the wall of the face of the tube. Enabling an individual to know the location of the laser will increase the efficiency of alignment of the laser to the face of the tubes and will increase the inspection rate and production of the tubes.

Referring to FIG. 7, because the light source 82 may only focus the light spot on a portion of the wall of the face 30 of tube 18, light source 82 may be manipulated by a motorized mechanism 88 to move light source 82 in a manner so that the light spot rotates around the circumference of the face 30 of tube 18, thereby enabling the entire face 30 of tube 18 to be inspected. For this embodiment, tube 18 remains stationary during the inspection process. Motorized mechanism 88, which is connected to light source 82 for manipulating or rotating light source 82, is connected to extendable member 84 for support of motorized member 88 during the inspection process. Preferably, as illustrated in FIGS. 1-4, because tube 18 is held in collet 22, which is already attached to motor 26 to rotate tube 18 during the cutting and finishing processes, tube 18 may be rotated by the gripping and rotating mechanism 16 and light source 82 may remain stationary during the inspection process.

Referring to FIG. 5, light source 82 comprises a transmitter 90 and an electrical receiver 92. Transmitter 90 and electrical receiver 92 may be a single unit manufactured by Keyence Corporation of America. Transmitter 90 is positioned near the face 30 of tube 18 and produces and directs light onto the face 30 of tube 18. Electrical receiver 92 is positioned near transmitter 90 and near the face 30 of tube 18. The light produced by transmitter 90 and directed onto the face 30 of tube 18 is reflected from the face 30 of tube 18. Electrical receiver 92 collects the reflected light that is deflected from the face 30 of tube 18. Electrical receiver 92 is connected to processing means 94 by a first electrical line 96. Electrical receiver 92 produces a first output, by converting the detected light to a corresponding electrical output representative of the topography of the face 30 of tube 18. The first output is transmitted through the first electrical line 96 to processing means 94. Processing means 94 may be capable of analyzing the collected light or first output from electrical receiver 92 to determine a height differential on the face 30 of tube 18. This height differential is indicative of a defect, such as a scratch, chatter, step, nick, burr or out of squareness on the face 30 of the cut and finished tube 18. Processing means 94 is attached to monitor 98 by a second electrical line 100. After analyzing the collected light or first output from electrical receiver 92, processing means 94 produces a second output. The second output is transferred to monitor 98. Monitor 98 may display the second output from processing means 94 in the form of a graph.

Figure 8:
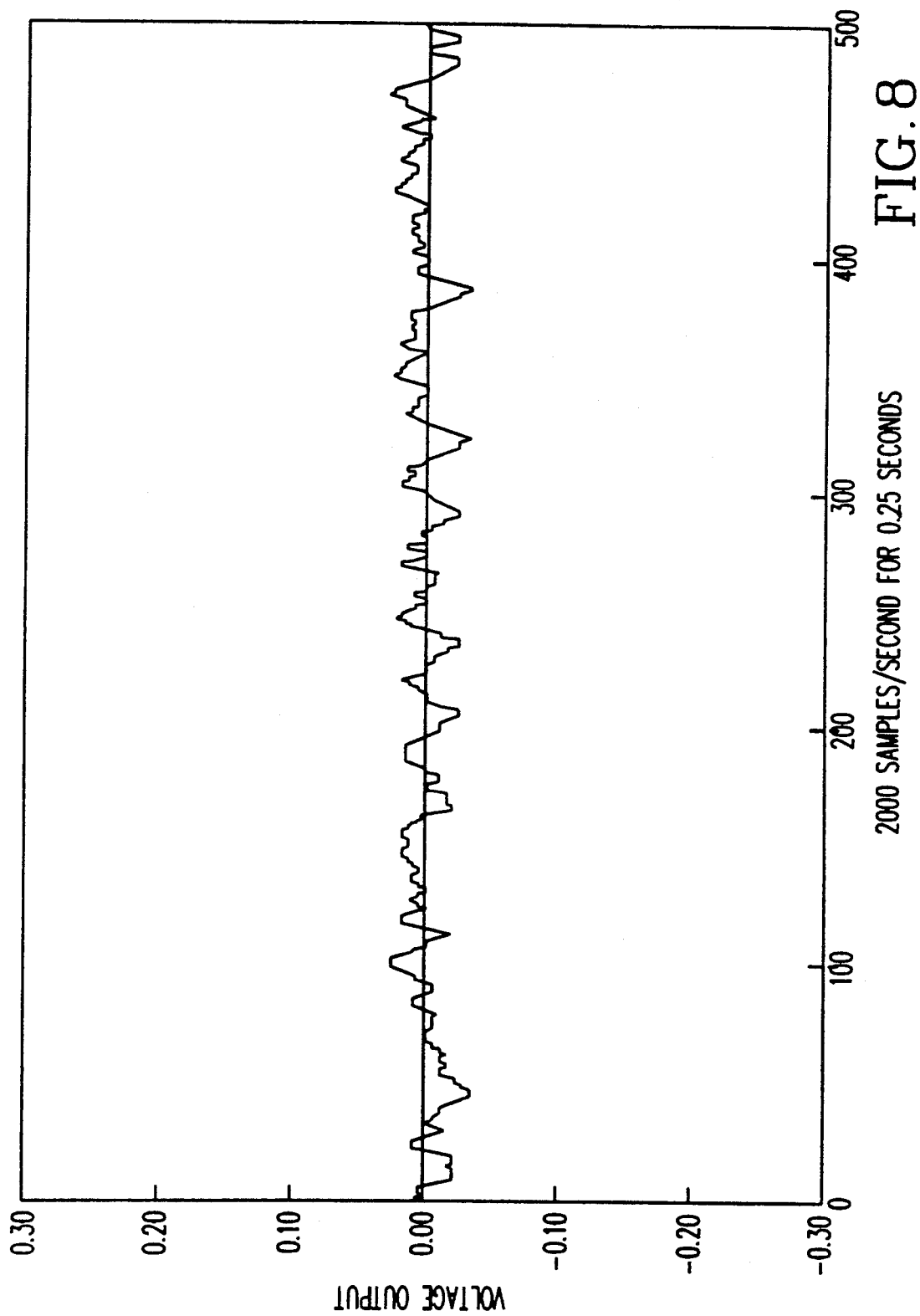
FIG. 8 is a graph displaying a typical response from the automatic laser inspection system for the face of a good tube.

Referring to FIG. 8, the graph displays the output of an inspection, utilizing the automatic laser inspection system 80, of a face of a tube with a good face.

Figure 9:
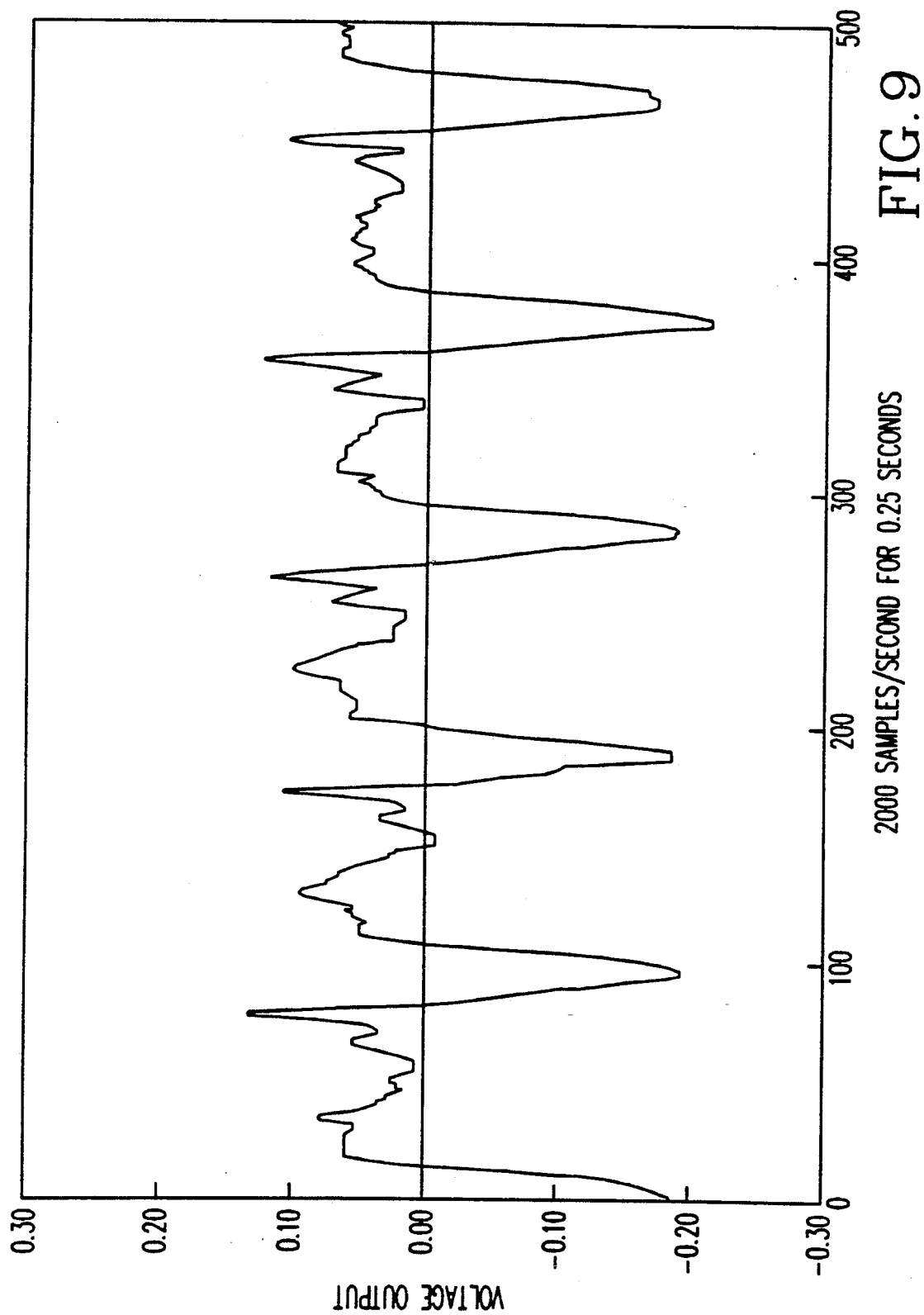
FIG. 9 is a graph displaying a typical response from the automatic laser inspection system for the face of a tube with a step defect.

Referring to FIG. 9, the graph displays the output of an inspection, utilizing the automatic laser inspection system 80, of a face of a tube with a step defect. As can be seen from FIG. 9, a specific pattern repeats over a period of time signifying a step defect. For each particular defect, such as a step, nick or chatter, a unique pattern repeats over a period of time signifying that particular defect. By recognizing the pattern, the type of defect can be determined. By determining the type of defect, that defect can be corrected.

As an example, light source 82 may be a laser using the well known method of triangulation to sense distance changes or the height differential on the face 30 of tube 18. The laser may have a visible radiation range of 670 nm. The wattage of the laser may be up to approximately 20 VA. The pulse rate of the laser may be up to approximately 40 kHz or 40,000 pulses per second. If tube 18 held by the gripping and rotating mechanism 16 is rotating at a motor speed of approximately 30 revolutions per second, then the laser will be inspecting the face 30 of tube 18 40,000 pulses per second as tube 18 rotates 30 revolutions per second. This number of inspections should provide ample data for displaying graphs of the output from the automatic laser inspection system 80, as illustrated in FIGS. 8 and 9. Because the laser may have a 40 kHz sampling frequency and a 16 kHz response frequency, the laser can accurately measure the height differential or distance changes on the face 30 of tube 18 rotating at high speed.

The pulse of the laser may be controlled by processing means 94. After the laser senses a distance change or the height differential on the face 30 of tube 18, the distance change or height differential may be translated into a voltage change for output to processing means 94. Processing means 94 can analyze either an analog voltage output or a digital output. By analyzing the output from electrical receiver 92, processing means 94 will be able to determine if a defect is present on the face 30 of tube 18. Processing means 94 may also be capable of pattern recognition, which is the ability to determine the type of defect, such as a step or nick, on the face 30 of tube 18. Processing means 94 can be programmed with predetermined data setting the acceptable limits of a good tube face. Processing means 94 may be able to compare the output from the automatic laser inspection system 80 with the preset acceptable limits programmed into processing means 94 and may be able to determine if tube 18 is acceptable as a tube with a good tube face or if tube 18 must be reworked through the cutting and finishing processes. If processing means 94 determines that the output from the automatic laser inspection system 80 is not within the acceptable limits of a good tube face, then processing means 94 may transmit a signal to monitor 98 indicating that tube 18 has a defective face and must be reworked. If processing means 94 determines that the output from the automatic laser inspection system 80 is within the acceptable limits of a good tube face, then processing means 94 may transmit a signal to monitor 98 indicating that tube 18 has a good face and that tube 18 has passed the inspection. This continuous on-line system will enable a tube to remain at one location for cutting, finishing and inspection. The tube will be accepted or rejected at the same location as cutting of the tube and finishing of the face of the tube. If rejected, the tube can be reworked at this same location and wasted time on transporting the tube throughout various locations in the manufacturing facility can be saved.

OPERATION

Referring again to FIG. 1, tube 18 is advanced by advancing mechanism 14 substantially parallel to track 20 and is received through collet 22. When solenoid 42 is activated, movable stop 44 extends to a predetermined distance from solenoid 42 up to the face 30 of tube 18 and pushes tube 18 through collet 22 to a desired position. Tube 18 is repositioned within collet 22 by the movable stop 44 pushing on the face 30 of tube 18. This repositioning aligns tube 18 with cutting bit 62 to enable tube 18 to be cut by cutting bit 62 to a desired length. Collet 22 grips tube 18 in this position.

Referring again to FIG. 2, movable stop 44 retracts back into solenoid 42 to a resting position. Tube 18 is rotated by a motor 26 attached to collet 22. Second mounting member 64 with the attached cutting bit 62 is slid along second base 66 toward tube 18 to position cutting bit 62 near tube 18 for the cutting and finishing processes.

Referring again to FIG. 3, cutting bit 62 has cut a piece of tube from tube 18. Cutting bit 62 may make a second cut to finish the face 30 of tube 18.

Referring again to FIG. 4, second mounting member 64 with the attached cutting bit 62 is slid backward away from tube 18 along second base 66 to a resting position. Extendable member 84 extends light source 82 over the top of the automatic stop mechanism 40 to a position within approximately 2" from the face 30 of tube 18.

Referring again to FIG. 5, light source 82 produces and directs light from transmitter 90 to the face 30 of tube 18. Tube 18 may be rotating and light source 82 stationary or tube 18 may be stationary and light source 82 rotating, to enable the entire face 30 of tube 18 to be inspected by the automatic laser inspection system 80. Electrical receiver 92 collects the light deflected from the face 30 of tube 18 and produces the first output. The first output is transferred from electrical receiver 92 to processing means 94 by electrical line 96, where the first output is analyzed. Processing means 94 produces a second output, which is transferred to monitor 44 by electrical line 100. Monitor 44 displays the second output. The second output may be a graph displaying a defect on the face 30 of tube 18 or a graph of a good tube face. The second output may also be the comparison of the predetermined data setting the acceptable limits of a good tube face with the output from the automatic laser inspection system 80.

If the analysis determines that a defect exists on the face 30 of tube 18, then tube 18 will have to be reworked through the automatic tube processing system 10. To rework tube 18, tube 18 may remain at the same location. As previously described, the cutting mechanism 60 may cut and finish the face 30 of tube 18 and the automatic laser inspection system 80 may inspect the face 30 of tube 18. This process will continue until the defect does not exist.

Therefore, the invention provides an automatic tube processing system and method utilizing an automatic laser inspection system for on-line inspection of the face of a tube during the manufacturing process of the tube.

We claim:

1. Apparatus for inspecting a face of a tube comprising:

a light source positioned near the face of the tube for transmitting light onto the face of the tube;

an electrical receiver positioned near the light source for detecting light reflected from the face of the tube and for converting the detected light to a first output representative of the topography of the face of the tube;

means for determining a height differential on the face of the tube for producing the first output; and manipulation means positioned near the tube for providing relative rotation between the tube and the light source.

2. The apparatus according to claim 1 wherein said manipulation means rotates the tube relative to the light source and the light source remains stationary.

3. The apparatus according to claim 2 wherein the manipulation means is a gripping and rotating mechanism comprising:

a collet for gripping the tube; and a motor connected to the collet for rotating the tube relative to the light source for monitoring several rotations of the face of the tube for each inspection of the tube.

4. The apparatus according to claim 1 wherein manipulation means rotates the laser relative to the tube and the tube remains stationary.

5. The apparatus according to claim 1 wherein the light source is a laser for inspecting the face of the tube.

6. The apparatus according to claim 5 wherein the laser is capable of focusing a visible light spot on the face of a wall of the tube for enabling an individual to visually observe the light spot on the face of the tube for accurate positioning of the laser.

7. The apparatus according to claim 5 wherein the laser further comprises a transmitter positioned near the face of the tube for producing and directing the light to the face of the tube.

8. The apparatus according to claim 5 wherein the laser comprises means for translation of the height differential on the face of the tube into voltage change for output to the processing means.

9. The apparatus according to claim 8 wherein the positioning of the laser is defined by a first vertical plane approximately along the centerline of the light source and a second vertical plane approximately along the longitudinal axis of the tube defining therebetween a first angle not to exceed approximately 5 degrees.

10. The apparatus according to claim 9 wherein the positioning of the laser is defined by a first horizontal plane approximately along the centerline of the laser and a second horizontal plane approximately along the longitudinal axis of the tube defining therebetween a second angle not to exceed approximately 45 degrees.

11. The apparatus according to claim 5 wherein the laser is positioned within approximately 2" from the face of the tube.

12. The apparatus according to claim 1 wherein the apparatus further comprises processing means, connected to the electrical receiver by electrical lines, for analyzing the first output from the electrical receiver and for producing a second output.

13. The apparatus according to claim 12 wherein the apparatus further comprises a monitor, connected to the processing means by electrical lines, for displaying the second output produced by the electrical receiver.

14. The apparatus according to claim 8 wherein the electrical receiver is a part of the laser.

15. The apparatus according to claim 1 wherein the tube is a nuclear fuel tube for containing nuclear fuel pellets.

16. The apparatus according to claim 1 wherein the tube is a guide thimble tube for providing structural support to a nuclear fuel assembly and for housing control rods within a nuclear reactor.

17. The apparatus according to claim 1 wherein the tube is an instrumentation tube for housing instruments within a nuclear reactor.

18. The apparatus according to claim 1 wherein the tube is an internal burnable absorber tube for containing internal burnable absorber rods to regulate power within a nuclear reactor.

19. An apparatus for preparing a face of a tube during a manufacturing process of the tube comprising:

manipulation means positioned near the tube for rotating the tube;

a laser, having a transmitter and an electrical receiver, positioned near the face of the tube, for transmitting light onto the face of the tube, for detecting light reflected from the face of the tube, and for producing a first output;

means for determining a height differential on the face of the tube for producing the first output;

processing means connected to the electrical receiver for analyzing the first output from the electrical receiver and for producing a second output;

a monitor connected to the processing means for displaying the second output form the processing means; and a movable stop arranged near the face of the tube for positioning the tube in a cutting position.

20. The apparatus according to claim 19 wherein the apparatus further comprises a cutting tool positioned near the tube for cutting the tube to a desired length.

21. The apparatus according to claim 20 wherein the cutting tool further comprises a facing tool for finishing the face of the tube.

22. A method for preparing a face of a tube during the manufacturing process of the tube comprising:

transmitting light from a light source positioned near the tube onto the face of the tube;

detecting the light reflected from the face of the tube in an electrical receiver positioned near the face of the tube;

providing relative rotation between the tube and the light source for inspecting the face of the tube; and determining a height differential on the face of the tube for producing a first output representative of the topography of the face of the tube.

23. The method according to claim 22 wherein the method further comprises focusing a visible light spot transmitted from a laser onto the face of the tube for enabling an individual to visually observe a light spot on the face of the tube.

24. The method according to claim 22 wherein the method further comprises:

rotating the tube relative to the light source for inspecting several rotations of the face of the tube;

cutting the tube to a desired length with a cutting tool positioned near the tube;

processing an output from the electrical receiver in the processing means; and displaying an output from the processing means on a monitor.

25. The method according to claim 22 wherein the method further comprises comparing the output with predetermined data for determining if the tube has a defect.

26. The method according to claim 22 wherein the method further comprises analyzing the output for recognizing a repeating pattern for determining a type of defect.

* * * * *